United States Patent
Pfistershammer

(10) Patent No.: US 7,235,055 B2
(45) Date of Patent: Jun. 26, 2007

(54) SAMPLING DEVICE INCLUDING TRANSPONDER FOR ELECTRONIC TRACKING AND IDENTIFICATION

(75) Inventor: Josef Pfistershammer, Claremont (AU)

(73) Assignee: AG-ID Pty Ltd., West Perth (AU)

( * ) Notice: Subject to any disclaimer, the term of this patent is extended or adjusted under 35 U.S.C. 154(b) by 0 days.

(21) Appl. No.: 10/522,580

(22) PCT Filed: Jul. 30, 2003

(86) PCT No.: PCT/AU03/00960

§ 371 (c)(1),
(2), (4) Date: Apr. 18, 2005

(87) PCT Pub. No.: WO2004/010773

PCT Pub. Date: Feb. 5, 2004

(65) Prior Publication Data

US 2005/0228310 A1    Oct. 13, 2005

(30) Foreign Application Priority Data

Jul. 30, 2002  (AU) .............................. 2002950452
Oct. 2, 2002   (AU) .............................. 2002951773

(51) Int. Cl.
*A61B 10/00*  (2006.01)
*A61B 17/00*  (2006.01)
*A61B 17/32*  (2006.01)
*A61B 17/34*  (2006.01)

(52) U.S. Cl. ...................... 600/567; 600/562; 600/564; 600/566; 606/116; 606/117; 606/167; 606/184; 606/185; 606/188

(58) Field of Classification Search ................ 600/562, 600/567; 606/116, 117
See application file for complete search history.

(56) References Cited

U.S. PATENT DOCUMENTS 3,224,434 A * 12/1965 Molomut et al. ........... 600/562
4,505,433 A *  3/1985 Selenke .................... 241/46.01

(Continued)

FOREIGN PATENT DOCUMENTS

DE          20022647        1/2002

(Continued)

*Primary Examiner*—Max Hindenburg
*Assistant Examiner*—Kristin D. Rogers
(74) *Attorney, Agent, or Firm*—Greenblum & Bernstein, P.L.C.

(57) ABSTRACT

A sampling device (10) characterised by a male portion comprising a male base portion (12) and a sample removal means (30), and a female portion comprising a first female base portion (14) and a sample container (16), the sample removal means (30) being removably located on the male base portion (12) and the sample container (16) being removably located at least in part within the first female base portion (14), wherein as the male and female portions are brought together the sample removal means (30) collects a biological sample (47) from an animal being tagged, is received through the first female base portion (14), and lodges in the sample container (16), this action in turn introducing the sample to a sample receiving space (74) within the sample container (16), pushing the sample container (16) from the first female base portion, and sealing the sample receiving space (74), the sample removal means (30) being provided with an amount of sample preparative or preservative (45) that is available to the sample (47) within the sample receiving space (74).

17 Claims, 3 Drawing Sheets

U.S. PATENT DOCUMENTS

| | | | | |
|---|---|---|---|---|
| 4,633,886 | A * | 1/1987 | Bucaro, Jr. | 128/749 |
| 4,694,781 | A * | 9/1987 | Howe et al. | 119/156 |
| 4,994,030 | A * | 2/1991 | Glowczewskie, Jr. et al. | 604/84 |
| 5,267,572 | A * | 12/1993 | Bucalo | 600/567 |
| 5,880,380 | A * | 3/1999 | Goldschmidt et al. | 73/863.85 |
| 6,080,173 | A * | 6/2000 | Williamson, IV et al. | 606/184 |
| 6,145,225 | A * | 11/2000 | Ritchey | 40/301 |
| 6,235,036 | B1 * | 5/2001 | Gardner et al. | 606/117 |
| 6,239,737 | B1 * | 5/2001 | Black | 342/51 |
| 6,968,639 | B2 * | 11/2005 | Destoumieux | 40/301 |
| 2003/0163141 | A1 * | 8/2003 | Malfanti et al. | 606/117 |
| 2004/0116940 | A1 * | 6/2004 | Brem | 606/117 |

FOREIGN PATENT DOCUMENTS

| | | |
|---|---|---|
| DE | 20101015 | 2/2002 |
| EP | 1060662 | 12/2000 |
| EP | 1060662 A1 * | 12/2000 |
| WO | 02/39810 | 5/2002 |
| WO | 02/078431 | 10/2002 |
| WO | WO 02/080661 A1 * | 10/2002 |
| WO | 03/034815 | 5/2003 |
| WO | 03/037075 | 5/2003 |

* cited by examiner

SAMPLING DEVICE INCLUDING TRANSPONDER FOR ELECTRONIC TRACKING AND IDENTIFICATION

FIELD OF THE INVENTION

The present invention relates to a sampling device and a method for its use. More particularly, the device and method of the present invention are intended for use in the simultaneous tagging of an animal and the collection of a biological sample therefrom.

BACKGROUND ART

There has long been the need for those in animal related industries (including the breeding of livestock, show animals, racing animals and other thoroughbreds) to be able to accurately identify individual animals, either for the purpose of authenticating the animal itself or for identifying the source of animal products and samples. Some of the more commonly used techniques include branding, tattooing, ear tags, ankle straps, chains and transponders, either injectable or on tags or straps. All of these techniques have different costs and success rates associated with them.

The identification of animals is important in many fields of endeavour, including medicine, research, breeding, quality control and environmental technologies. DNA analysis is one technique available for the identification of animals. Identification by way of DNA analysis generally requires removal of a biological sample from the animal and "off-site" laboratory analysis of the sample. Recent cases of infected or contaminated meat products has increased the need to be able to sample large numbers of animals and accurately associate each sample with its source. Furthermore, there is also the need to make this association difficult to break or to be interfered with, so that the source of samples can be correctly and confidently identified.

Modem DNA analysis techniques can be performed on very small samples and can be conducted very quickly. Presently, quality control of biological material and the preparation of genetic genealogy of animals are conducted to an increasing degree with huge numbers of samples. DNA analysis is very sensitive and impurities must be excluded. Furthermore, there is an on-going need to protect samples from DNA-degrading enzymes.

There are many ways of obtaining a sample of DNA from animals. For example, taking biological samples for DNA analysis can involve blood sampling. A skilled practitioner, for example, a vet, is needed for this method of sampling which can become very expensive, especially for large populations.

In cattle breeding, it is known to remove hairs and hair roots and place them into a sample container which is then labelled manually to identify the source of the biological material. This process can be time consuming and there are a number of potential problems that are particularly related to the degree of training of the sampler. These include the potential for falsification of samples, either intentionally or accidentally. Intentional falsification may include the deliberate mislabelling of a sample or placing a sample from one source into a sample container that identifies the sample as having been sourced from a different animal. The above examples of falsification can also occur accidentally.

There is a need for a sampling device that is able to simultaneously register an animal (e.g. provide an identification means such as an ear tag) and take a sample of tissue for analysis, whilst providing a sample container that minimizes the potential for intentional or accidental falsification of samples.

The sampling device of the present invention has one object thereof to overcome substantially the above-mentioned problems associated with the prior art, or at least provide a useful alternative thereto.

The preceding discussion of the background art is intended to facilitate an understanding of the present invention only. It should be appreciated that the discussion is not an acknowledgement or admission that any of the material referred to was part of the common general knowledge in Australia as at the priority date of the application.

Throughout the specification, unless the context requires otherwise, the word "comprise" or variations such as "comprises" or "comprising", will be understood to imply the inclusion of a stated integer or group of integers but not the exclusion of any other integer or group of integers.

DISCLOSURE OF THE INVENTION

In accordance with the present invention there is provided a sampling device characterised by a male portion comprising a male base portion and a sample removal means, and a female portion comprising a first female base portion and a sample container, the sample removal means being removably located on the male base portion and the sample container being removably located at least in part within the first female base portion, wherein as the male and female portions are brought together the sample removal means collects a biological sample from an animal being tagged, is received through the first female base portion, and lodges in the sample container, this action in turn introducing the sample to a sample receiving space within the sample container, pushing the sample container from the first female base portion, and sealing the sample receiving space, the sample removal means being provided with an amount of sample preparative or preservative that is available to the sample within the sample receiving space.

The male base portion preferably comprises a base and an upstanding member, the upstanding member having provided thereon an annular lip such that the lip prevents the male portion being pulled from the first female base portion once received therein.

The sample removal means is preferably adapted to be positively located on the upstanding member prior to the connection of the male and female portions.

The sample removal means preferably comprises a generally cylindrical cutter means and a thrust member the cutter means having an open upper end provided with a cutting edge to facilitate penetration of animal tissue, the thrust member is received within a bore of the cutter means and has a seat member provided therein to seat the upstanding member.

The thrust member further preferably defines therein a chamber adjacent the open upper end of the cutter means such that the biological sample obtained thereby presses into the chamber. The chamber has provided therein an amount of biological sample preparative or preservative, preferably in substantially granular form, such that when the sample removal means is received within the sample container the preparative or preservative is available to the biological sample also retained within the sample container. The chamber has provided thereover a sheet of porous material so as to retain the preparative or preservative therein whilst allowing it to function with respect to the sample ultimately retained within the sample container.

The thrust member preferably engages the cutter means within the bore thereof such that thrust imparted to the thrust member is passed to the cutter means.

Preferably, the cutter means is tapered from lower end to upper end, thereby facilitating its passage into the female portion of the sample device and its retention within the sample container. The sample container is also tapered, such that it is broader at an open lower end thereof than it is at an upper end thereof, the lower end being received within the first female base portion before the male and female portions are brought together.

In one form of the present invention the first female base portion comprises a base member, in which is provided a frangible portion through which the male portion may be received and retained in part, and an upstanding collar, the upstanding collar is spaced radially apart from the aperture and is adapted to receive thereon a cap.

Preferably, the open lower end of the sample container is releasably retained within the upstanding collar of the first female base portion by the cap, whereby the sample container is received through an aperture provided in the cap and as the sample removal means is received in the open lower end of the sample container and pushed as the male and female portions are brought together, the sample container and sample removal means detach from their respective portions leaving the remainder thereof positively engaged.

Still preferably, a ring of resilient material is captured within the upstanding collar and cap, the ring being of broader dimension than the aperture in the base member of the first female base portion and the aperture in the cap, whereby the ring is pushed upwardly by the annular lip of the upstanding member as the male and female portions are brought together, such that an attempt to tamper with the upstanding member should be visible.

The sampling device may further comprise a transponder. The transponder is preferably provided as a separate member closely associated with the base member of the first female base portion, the transponder having provided therein an aperture to cooperate with the aperture provided in the first female base portion.

Preferably, a second female base portion is provided to sandwich the transponder between it and the first female base portion, the second female base portion having an aperture provided therein to cooperate with the frangible portion and aperture of the first female base portion and transponder, respectively.

Still preferably, both the male portion and female portion have a matching or otherwise coordinated identification means provided thereon, the identification means being such that it will be evident should an attempt be made to obscure, obliterate or remove the identification. An identification means is preferably provided on each of the first female base portion, the sample container and the male base portion.

In accordance with the present invention there is further provided a sampling device characterised by a male portion comprising a base and an upstanding member, and a female portion comprising a first female base portion, the upstanding member having an annular lip arranged to be retained within the female portion when the male and female portions are brought together, the first female base portion further comprising an upstanding collar and cap, the cap having provided therein an aperture, whereby the annular lip of the upstanding member is retained within the collar and cap together with a resilient ring, the resilient ring preventing at least partially any attempt to interfere with the upstanding member and thereby separate the male and female portions.

In accordance with the present invention there is still further provided a sampling device and tagging system characterised in that it includes as basic components a male portion comprising a base and upstanding member, and a female portion comprising a first female base portion, cap and a resilient ring retained thereby, wherein as the male and female portions are brought together the upstanding member is received through or in the first female base portion in a positive and generally unreleasable manner, the resilient ring and cap being arranged so as to prevent any undetectable interference with the upstanding member in an effort to release the male and female portions, the system allowing for the addition of one or more transponders for electronic identification purposes, and the use of sampling components.

Preferably, the sampling components comprise a sample removal means and a sample container, the sample removal means being releasably located on the upstanding member and the sample container being releasably located on the female portion, wherein the action of bringing the male and female portion together obtains a biological sample from an animal and tags that animal simultaneously, the sample removal means further providing an amount of sample preparative or preservative for the collected biological sample.

BRIEF DESCRIPTION OF THE DRAWINGS

The present invention will now be described, by way of example only with reference to two embodiments thereof and the accompanying drawings, in which.

BEST MODE(S) FOR CARRYING OUT THE INVENTION

Figure 1:
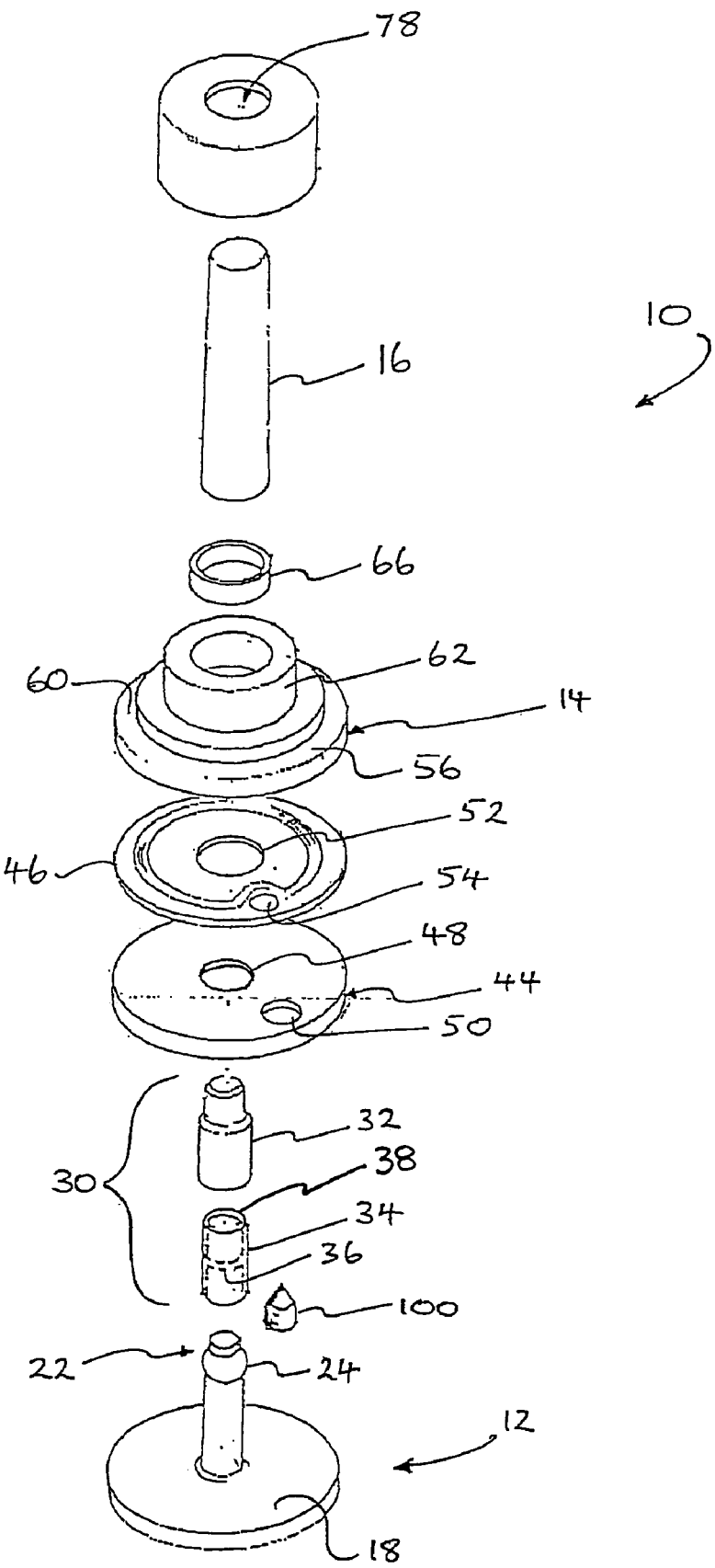
FIG. 1 is an exploded upper perspective view of a sampling device in accordance with a first embodiment of the present invention.
Figure 2:
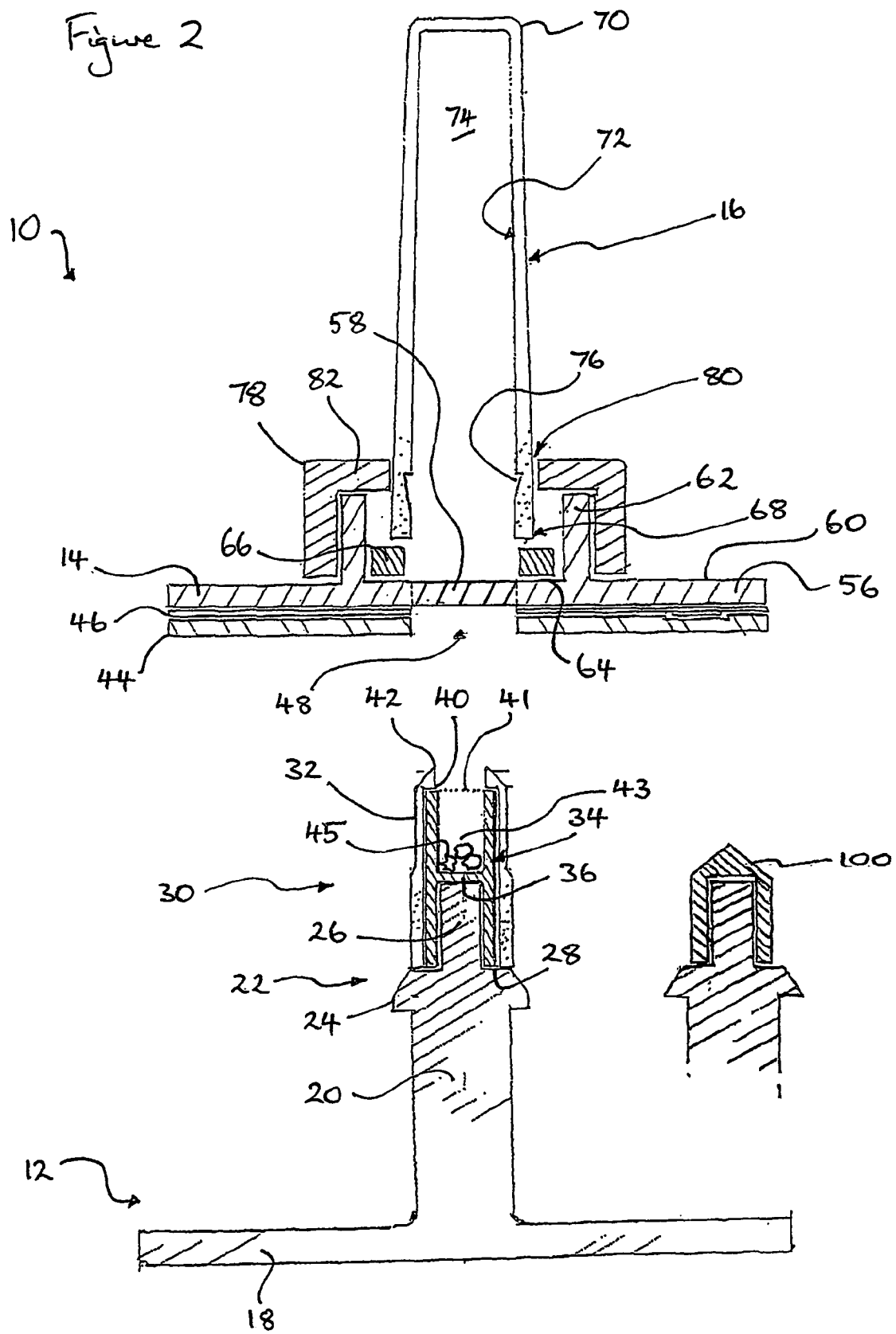
FIG. 2 is a cross-sectional view through the sampling device of FIG. 1, showing the male and female portions of the sampling device separately prior to the tagging of an animal and the collection of a biological sample therefrom.
Figure 3:
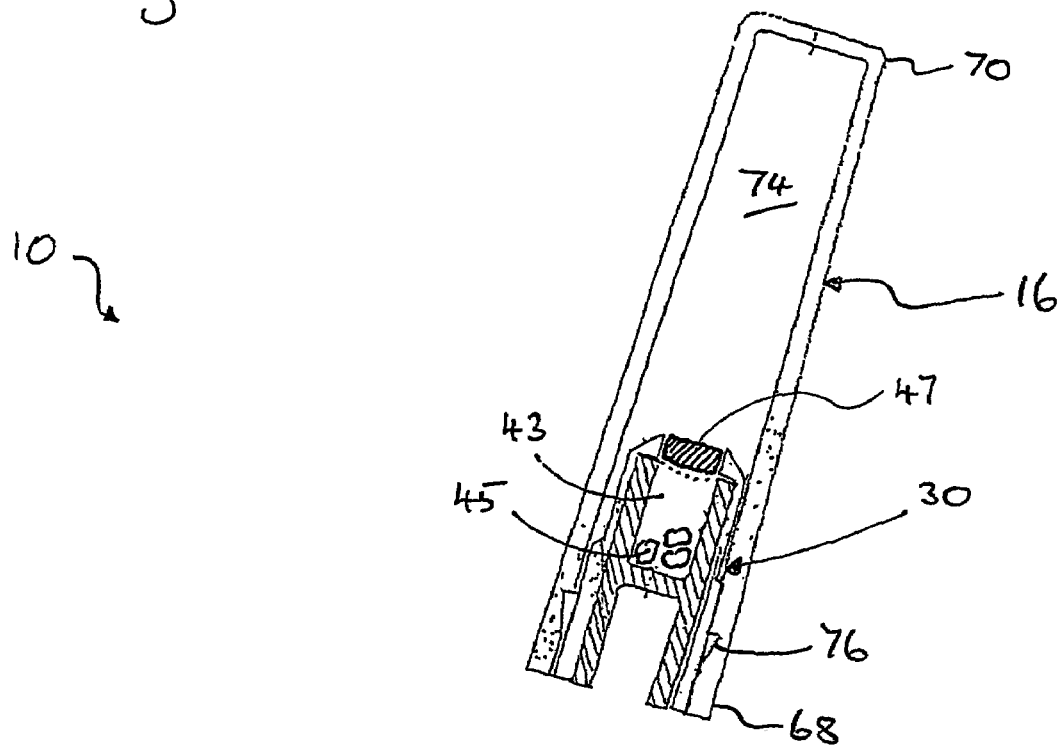
FIG. 3 is a cross-sectional view of the sampling device of FIG. 1, showing the sample device after application to an animal and the collection of a biological sample, with the sample container having been separated from the female portion after collection of the biological sample.
Figure 3:
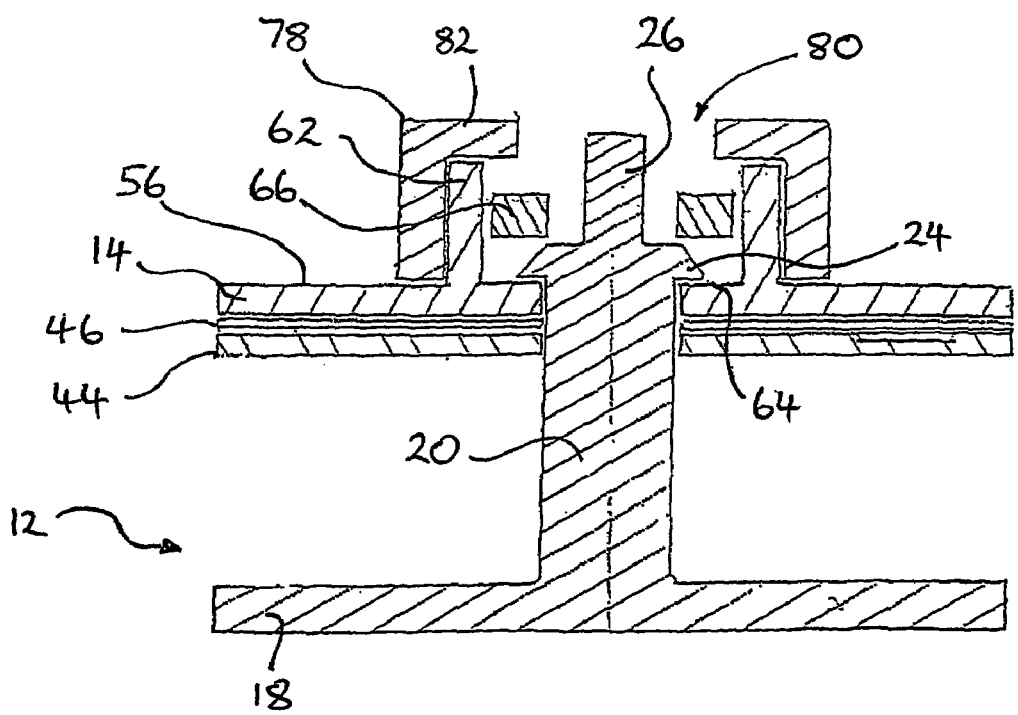

In FIGS. 1 to 3 there is shown a sampling device 10 in accordance with a first embodiment of the present invention, the sampling device 10 comprising a male base portion 12, a first female portion 14 and a sample container 16.

The male base portion 12 comprises a substantially flat, circular base 18, from the centre of which projects an upstanding shaft 20. The shaft 20 has provided at an upper end 22 thereof an annular lip 24. A locating spigot 26 projects upwardly beyond the annular lip 24 and a locating shoulder 28 is provided therebetween. The locating spigot 26 is generally cylindrical but is of smaller diameter than the upstanding member 20, which is also of generally cylindrical configuration.

A sample removal means 30 is seated on both the locating spigot 26 and locating shoulder 28 of the male base portion 12, as best seen in FIG. 2. The sample removal means 30 comprises a generally cylindrical steel cutter means 32 and a generally cylindrical thrust member 34. The cutter means 32 is made of steel due to the need to retain a sharp edge thereon. The thrust member 34 is generally hollow but does have provided extending thereacross a seat member 36. The seat member 36 rests on and abuts the locating spigot 26, whilst lower ends of both the cutter means 32 and the thrust member 34 abut and rest on the locating shoulder 28 of the upstanding member 20.

The thrust member 34 is initially located within the bore of the cutter means 32. An upper end 38 of the thrust member 34 abuts a forward shoulder 40 of the cutter means 32. A cutting edge 42 is provided on an upper end of the cutter means 32, adjacent the forward shoulder 40, again as is best seen in FIG. 2. The cutter means 32 is provided with a wider diameter nearer the lower end thereof, with a tapering of its diameter about the middle thereof to a marginally narrower diameter. At a point adjacent the forward shoulder 40, which is provided in the bore of the cutter means 32, the outer surface of the cutter means 32 tapers inwardly to form the cutting edge 42.

A sheet of porous material, for example gauze 41 is provided over the upper end 38 of the thrust member 34, thereby creating a chamber 43. An amount of granular sample preparative and/or preservative is provided in the chamber 43, for example rock salt 45 which is appropriate due to its granular nature and hydroscopic properties. The gauze 41 is retained in position by the cutter means 32 and it retains the rock salt 45 in the chamber 43.

The male base portion 12, the upstanding member 20 and the sample removal means 30 comprise a male portion of the sampling device 10.

The sampling device 10 further comprises a second female base portion 44 and a transponder 46. The second female base portion 44 is generally circular, having a centrally provided aperture 48, best seen in FIG. 1. A recess 50 is provided adjacent a periphery of the second female base portion 44.

The transponder 46 is again substantially circular and planar, having a central circular aperture 52 provided therein. At least a portion of the electronics thereof is provided in a raised portion 54 that is arranged to interact with and engage the recess 50 provided in the second female base portion 44, as is best seen in FIG. 2.

The transponder 46 is sandwiched between the second female base portion 44 and the first female base portion 14. The first female base portion 14 is of generally the same circular dimensions as both the second female base portion 44 and the transponder 46. The first female base portion 14 comprises a substantially flat base member 56, in which is provided a centrally located circular frangible portion 58, which is effectively contiguous with the aperture 52 provided in the transponder 46 and the aperture 48 of the second female base portion 44.

The base member 56 of the first female base portion 14 has provided on an upper surface 60 thereof an upstanding circular collar 62. The upstanding collar 62 is generally co-axial with the frangible portion 58 but is spaced radially apart therefrom so as to create a shoulder 64 therebetween, as is best seen in FIGS. 2 and 3. A locking ring 66 is provided so as to be located on the shoulder 64 and is again generally co-axial with the frangible portion 58, aperture 52, and aperture 48. A lower end 68 of the sample container 16 is located "on top of" the locking ring 66, within the upstanding collar 62. The sample container 16 is provided in the form of a tapered cylinder, enclosed at its upper most end 70. The lower end 68 is open and is broader than the upper end 70. The sample container 16 is provided with an internal surface 72 defining a sample receiving space 74, best seen in FIGS. 2 and 3. The internal surface 72 has provided therein an annular recess 76 generally adjacent the lower end 68 of the sample container 16.

A cap 78 is received over the sample container 16 and the upstanding collar 62, as shown in FIG. 2, and is fixed thereto, for example by way of ultrasonic welding. The sample container 16 projects almost entirely through an aperture 80 provided in the upper surface 82 of the cap 78. Importantly, the aperture 80 is of narrower diameter than the lower end 68 of the sample container 16 such that the sample container 16 is held in position with respect to the first female base portion 14. Further, if the sample container 16 were to be removed from the cap 78 it can not be reinserted due to its width at its open lower end 68.

The first female base portion 14, the locking ring 66, the cap 78 and the sample container 16 comprise a female portion of the sampling device 10. However, as noted hereinafter, the sample container 16 may not be present/ necessary in certain embodiments of the present invention.

In use, a user (not shown) wishing to sample tissue from an animal (not shown) and to tag that animal fits the male base portion 12 with the sample removal means 30 provided thereon to a first part of a tagging gun (not shown). Similarly, the remainder of the sampling device 10 is fitted to a second portion of the tagging gun, the portion of the animal to be tagged is then placed between the first and second portions of the tagging gun and the tagging gun actuated so that the two separate portions of the sampling device 10 are brought together. During this process the cutter means 32 pierces the portion of the animal to be tagged, for example an ear, punching out a generally circular portion of tissue as the cutter means 32 impinges upon the frangible portion 58 of the first female base portion 44. The frangible portion 58 of the first female base portion 44 resists the pressure initially so as to facilitate the punching out of a tissue sample but gives way ultimately under that pressure, thereby bringing the two portions of the sampling device 10 together as the male base portion 12 presses upwardly into the remainder of the female portion of the sampling device 10. If the frangible portion 58 of the first female base member 14 were not present it is envisaged that the cutter means 32 may be inclined to simply push through the animal tissue, thereby not obtaining a sample.

Specifically, the sample removal means 30 is pushed through the second female base portion 44, through the transponder 46 and through the first female base portion 14, whereby the sample removal means 30 is pressed into the lower end 68 of the sample container 16 and firmly wedged therein. Further, the annular lip 24 of the upstanding member 20 is also pushed upwardly through the second female base portion 44, through the transponder 46 and through the first female base portion 14. The annular lip 24 pushes the locking ring 66 upwardly towards the cap 78. This same process of the annular lip 24 pushing upwardly ejects the sample container 16 from the cap 78, the annular recess 76 allowing some inward flexing of the lower end 68 of the sample container 16 whereby it can pass through the aperture 80 provided in the cap 78, thereby assuming the separated arrangement shown in FIG. 3.

As a result of the tagging operation a tissue sample 47 from the tagged animal has been collected within the sample receiving space 74 of the sample container 16, in which it is in close association with the rock salt tissue preparative/ preservative housed in the chamber 43 of the thrust member 34. The sample removal means 30 is received within the sample container 16 in a manner so as to form a substantially fluid impermeable seal by way of an interference fit. The sample container 16 together with the sample removal means 30 and the entrained tissue sample 47 are then able to be transferred for analysis.

The sample container 16 and the first female base portion 14 of the sampling device 10 are both labelled with an identification means (not shown) so as to clearly identify the source of the sample to be taken. For example, the identification means may comprise a series of numbers and/or letters that serve to identify a particular animal. This labelling preferably may not be removed without damaging the sample container 16 or the reminder of the female portion of the sampling device 10, for example the first female base portion 14. Any sampling device 10 having a damaged sample container 16 and/or remainder of the female portion thereof will not have any resulting sample taken analysed.

Further, once the sample removal means 30 has been forced into the sample container 16 and the sample container 16 forced from the cap 78, the sample container 16 may not be reinserted through the cap 78 without damaging the sample container 16, again due to the breadth of the lower end 68 of the sample container 16, particularly after insertion of the sample removal means 30 therein.

Once the sampling device 10 has been fitted to the tagged animal the annular lip 24 of the upstanding member 20 is unable to be withdrawn through the apertures in any of the first female base portion 14 (as a result of the removal of the frangible portion), the transponder 46 and the second female base portion 44, without damage to the device 10 which would prevent reuse and signal tampering.

The base 18 of the male base portion 12 also has identification means (no shown) provided thereon that is/are unable to be removed without damage. This labelling will be chosen to correspond with or coordinate with labelling referred to hereinabove as provided on the sample container 16 and first female base portion 14, providing a further check of the integrity of the sampling process.

It is envisaged that further embodiments of the present invention may be provided. A second embodiment of the present invention provides a sampling device substantially in accordance with the sampling device 10 but neither of the second female base portion 44 or the transponder 46. This provides a sampling device that obtains an animal tissue sample in an identical manner to that of the sampling device 10 but does not provide the additional electronic identification means provided by the transponder 46. The second female base portion 44 that is provided in the sampling device 10 to protect and locate the transponder 46 is consequently also not necessary.

The locking ring 66 is preferably formed of a resilient or strong material, for example steel or hardened plastics materials. It is intended that the locking ring 66 be tougher than the surrounding materials, for example the cap 78 and the upstanding member 20, such that interference therewith will be clearly evident.

Still further, a tamper-proof animal identification device may be provided by replacing the sample removal means 30 with a simple sharpened tip 100, as shown in the alternative in FIGS. 1 and 2. The sample container 16 of the sampling device 10 is not necessary in this embodiment of the invention and the presence of the second female base portion 44 and the transponder 46 is dependent only upon whether electronic identification is required as an option. As such, the anti-tampering properties of the sampling device 10 are retained in this third embodiment of the invention, without any of the tissue sampling properties.

While advantageous and preferred embodiments of the present invention have been selected and described as illustrations of the invention, it should be understood by those skilled in the art that changes and adaptations can be made therein without departing from the scope of the invention.

The invention claimed is:

1. A sampling device comprising:
    a male portion comprising a male base portion and a sample removal system, and
    a female portion comprising a first female base portion and a sample container,
    the sample removal system being removably located on the male base portion and the sample container being removably located at least in part within the first female base portion,
    the sample removal system being adapted to collect a biological sample from an animal being tagged as the male and female portions are brought together and in turn to be received within, and to seal the biological sample therein providing a sealed sample receiving space defined within the sample container, the sample removal system having provided therein an amount of sample preparative or preservative that is available to the biological sample within the sealed sample receiving space,
    wherein the sample container is held with the first female base portion such that as the male and female portions are brought together the thereby sealed sample container is pushed from the female portion, and wherein further the male base portion the first female base portion so brought together may not be separated without damage to the device.

2. The sampling device of claim 1 wherein the male base portion comprises a base and an upstanding member, the upstanding member having provided thereon an annular lip such that the lip prevents the male portion being pulled from the first female base portion once received therein.

3. The sampling device of claim 2 wherein the sample removal system is adapted to be positively located on the upstanding member prior to the connection of the male and female portions.

4. The sampling device of claim 1 wherein the sample removal system comprises a generally cylindrical cutter and a thrust member, the cutter having an open upper end provided with a cutting edge to facilitate penetration of animal tissue and the thrust member is received within a bore of the cutter and has a seat member provided therein to seat an upstanding member provided on the male base portion.

5. The sampling device of claim 4 wherein the thrust member further defines therein a chamber adjacent the open upper end of the cutter such that the biological sample obtained thereby presses into the chamber.

6. The sampling device of claim 5 wherein the sample preparative or preservative is provided in substantially granular form, the chamber having provided thereover a sheet of porous material so as to retain the preparative or preservative therein whilst allowing it to function with respect to the sample ultimately retained within the sample container.

7. The sampling device of claim 4 wherein the thrust member engages the cutter within the bore thereof such that thrust imparted to the thrust member is passed to the cutter.

8. The sampling device of claim 4 wherein the cutter is tapered from lower end to upper end, thereby facilitating its passage into the female portion of the sample device and its retention within the sample container.

9. The sampling device of claim 1 wherein the sample container is tapered such that it is broader at an open lower end thereof than it is at an upper end thereof, the lower end being received within the first female base portion before the male and female portions are brought together.

10. The sampling device of claim 1 wherein the first female base portion comprises a base member, in which is provided a frangible portion through which the male portion may be received and retained in part, and an upstanding collar, the upstanding collar is spaced radially apart from the aperture and is adapted to receive thereon a cap.

11. The sampling device of claim 10 wherein the open lower end of the sample container is releasably retained within the upstanding collar of the first female base portion by the cap, whereby the sample container is received through an aperture provided in the cap and as the sample removal system is received in the open lower end of the sample container and pushed as the male and female portions are brought together, the sample container and sample removal system detach from their respective portions leaving the remainder thereof positively engaged.

12. The sampling device of claim 10 wherein a ring of resilient material is captured within the upstanding collar and cap, the ring being of broader dimension than the aperture in the base member of the first female base portion and the aperture in the cap, whereby the ring is pushed upwardly by the annular lip of the upstanding member as the male and female portions are brought together, such that an attempt to tamper with the upstanding member should be visible.

13. The sampling device of claim 1 wherein the sampling device further comprises a transponder.

14. The sampling device of claim 13 wherein the transponder is provided as a separate member closely associated with the base member of the first female base portion, the transponder having provided therein an aperture to cooperate with the aperture provided in the first female base portion.

15. The sampling device of claim 14 wherein a second female base portion is provided to sandwich the transponder between it and the first female base portion, the second female base portion having an aperture provided therein to cooperate with the aperture of the transponder and the frangible portion of the first female base portion.

16. The sampling device claim 1 wherein both the male portion and female portion have a matching or otherwise coordinated identification device provided thereon, the identification device being configured such that it will be evident should an attempt be made to obscure, obliterate or remove the identification.

17. The sampling device of claim 16 wherein an identification device is provided on each of the first female base portion, the sample container and the male base portion.

* * * * *